United States Patent [19]
Stanford

[11] 4,095,595
[45] Jun. 20, 1978

[54] NON WOVEN ROLLED BANDAGE

[76] Inventor: Ralph B. Stanford, 130 Ridgewood Rd., Radnor, Pa. 19087

[21] Appl. No.: 758,829

[22] Filed: Jan. 12, 1977

[51] Int. Cl.² ............................................. A61L 15/00
[52] U.S. Cl. .................................. 128/156; 428/192; 428/296
[58] Field of Search ............... 128/155, 156, 157, 170, 128/171, 169; 428/192, 296

[56] References Cited

U.S. PATENT DOCUMENTS

| | | | |
|---|---|---|---|
| 3,510,389 | 5/1970 | Olson | 428/296 X |
| 3,536,072 | 10/1970 | Quello | 128/156 X |
| 3,661,674 | 5/1972 | Higgs et al. | 428/296 X |
| 3,683,921 | 8/1972 | Brooks et al. | 128/156 X |
| 3,772,136 | 11/1973 | Workman | 128/156 X |
| 3,788,936 | 1/1974 | Brock et al. | 428/296 X |

Primary Examiner—John D. Yasko
Attorney, Agent, or Firm—Bailey, Dority & Flint

[57] ABSTRACT

A rolled bandage for use in the medical field is illustrated constructed of a foraminous spun bonded strip which has slit edges and wound under tension wherein the strip is formed of spaced continuous extruded cellulose filaments each having portions extending alternately in lengthwise and crosswise directions with loop portions between fuse bonded intersections of the lengthwise and crosswise portions.

5 Claims, 2 Drawing Figures

NON WOVEN ROLLED BANDAGE

BACKGROUND OF THE INVENTION

Rolled bandages have been typically made of woven absorbent cotton gauze, slit in the proper width and supplied in rolls 5 or 10 yards long, wrapped and packaged in fiber board boxes. Typical thread counts are 44 threads in the warp by 40 threads in the filling. Thread counts this high have generally been necessary so that the interticies are small enough to provide sufficient cover preventing gross dirt from passing through the structure and onto a wound or primary dressing surface. Further, with this density of yarns it is possible to prevent or reduce ravelling by compressing the edge of a damp bandage just prior to slitting to hammer down the warp threads into intimate contact with the filling. This does, however, allow some linting of the partially destroyed crushed fibers and contamination off the wound.

These high count woven bandages have several disadvantages in that under the normal stress of bandaging, they do not stretch and, hence, cannot conform to the irregular contours of the limb, arm, finger, toe, or other part of the body they are being used upon. Furthermore, because they are composed of densely packed cotton fibers inside of yarns, there is but little space for body exidates and they are characterized by relatively low absorbency.

To overcome the disadvantages of these traditional bandages, woven elastic bandages have been made which exhibit better conformability. These are generally made by immersing low count woven gauze fabric in a mercerizing solution which causes considerable shrinkage upon washing and drying, the fabric remains in its shrunken state and hence, can be stretched under tension to almost its original dimensions. Such procedures and fabrics are illustrated in U.S. Pat. Nos. 2,379,574 and 2,404,837. In order to impart elasticity by this procedure, it is necessary to use a very low thread count, characteristically 14 × 10 per inch. Tightly woven gauzes do not shrink sufficiently to provide high enough elasticity because of the lack of mobility of the yarns. Articles of commerce made by this procedure characteristically finish out at a count of 16 by 14. The absorbency of these woven elastic bandages are, therefore, necessarily quite low because they share the disadvantage of all fibers being tightly woven in yarns as is the case with woven high count bandages but in addition there are less yarns to the inch. Further, because of the very open mesh structure of the finished bandage, there is far less protection of the wound from contamination by outside sources. A further disadvantage is that, with this very low yarn count, it is impossible to prevent ravelling by the compressive method used on high count fabrics. Indeed, if the edges are compressed, and some transient bonding occurs between warp and filling yarns, this bond is broken upon the application of stress in order to secure product conformability and the crushed fibers drop off in the form of lint with resultant contamination of the wound area. In an effort to overcome this disadvantage, a far more complicated slitting procedure has been employed. The elastic gauze must be slit then run over a folding plate to produce what is known as a "C" fold and then wound into finished form.

BRIEF DESCRIPTION OF THE INVENTION

Accordingly, it is an important object of this invention to eliminate many of the aforementioned disadvantages of rolled bandages made from a high count absorbent cotton or shrunken cotton elastic material. In place of short staple fibers which must be twisted into yarns then woven into fabrics with all of the above mentioned disadvantages, it has been found that a spun bonded non woven with continuous filaments of hydrophilic polymer may be utilized. Non Wovens have been thought to be unacceptable for use in rolled bandages because adhesives usually employed are incompatible with bandages and spun bonded non wovens are normally still inelastic and lack sufficient absorbency. Suitable non wovens may be made however, by extruding a liquid form of the fiber forming material, preferably cellulose polymer, through spinerettes, while depositing them on a moving screen. While still plastic, these individual filaments are compressed to form a foraminous web by fused bonding all points of intersection. Upon solidification or regeneration as in the case of a solution of cellulose, a non woven fabric of sufficient integrity can be formed. Most important to this invention is that the speed of the moving belt must be regulated relative to the rate of spinning so that the fibers are overfed on the screen forming sinos looped or crimped filaments relative to each other. These loops are controlled to give the predetermined elasticity and strength to the finished fabric. After washing, if necessary, and drying, the non woven fabric is ready for slitting by conventional means and rolling to form finished bandages. It is not necessary to compress the edges because there are no yarns which can ravel. A suitable spun bonded non woven material, known to have excellent blood absorption properties when used as topical sponges, is illustrated in U.S. Pat. No. 3,906,130.

It has been found that a useful bandage may advantageously be made when the total weight of the filaments in 1 square meter of the fabric is in the range of from 20 to 40 grams per square meter. Fabrics of weight less than this have insufficient strength and above this weight, they are too bulky and of disproprotionate strength. Elasticity in both directions is desirable and for bandaging it is preferable that a higher percentage of elasticity be in the crosswise direction rather than in the lengthwise direction.

BRIEF DESCRIPTION OF THE DRAWING

The construction designed to carry out the invention will be hereinafter described, together with other features thereof.

The invention will be more readily understood from a reading of the following specification and by reference to the accompanying drawing forming a part thereof, wherein an example of the invention is shown and wherein.

DESCRIPTION OF A PREFERRED EMBODIMENT

Figure 1:
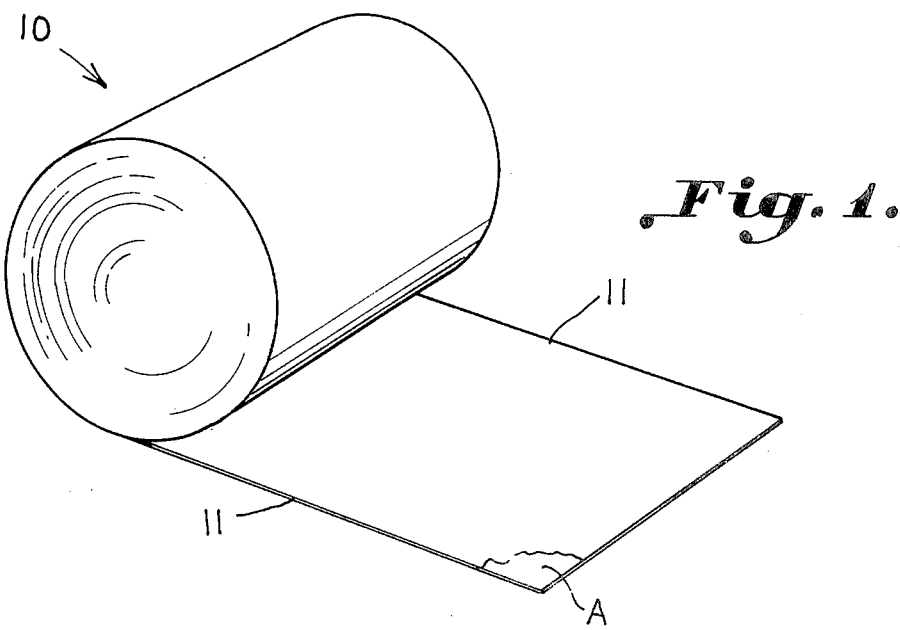
FIG. 1 is a perspective view of a rolled bandage constructed in accordance with the present invention.
Figure 2:
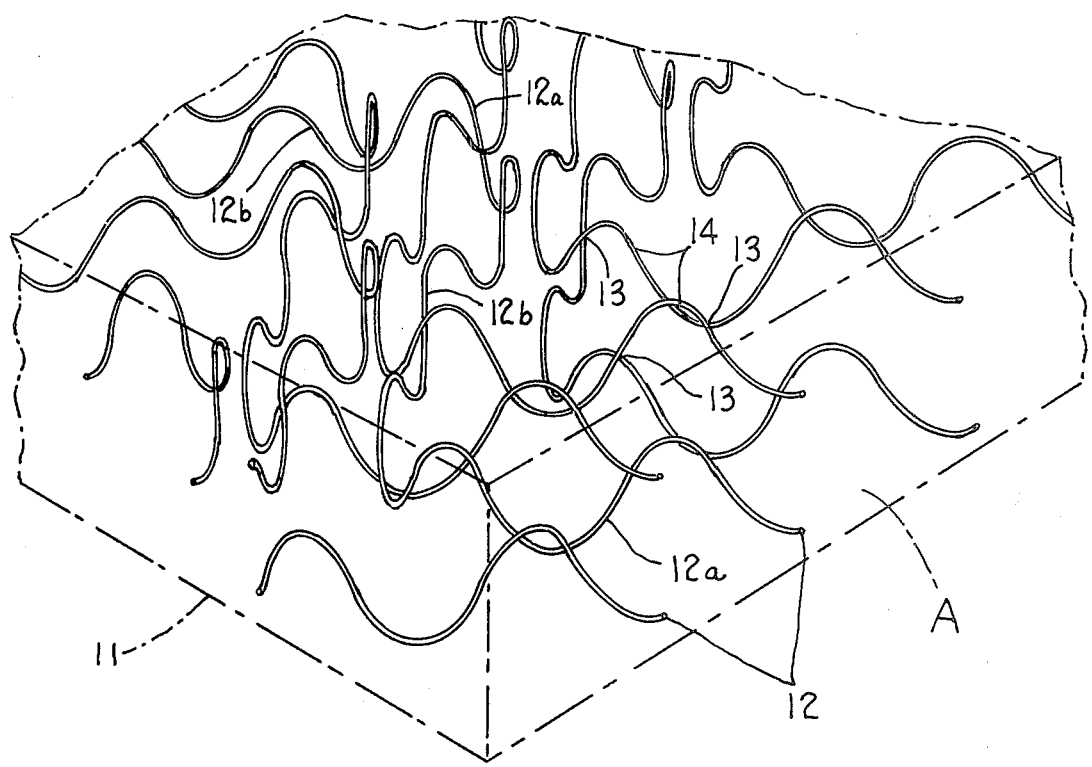
FIG. 2 is a greatly enlarged perspective view of a corner of the bandage, broken away at A in FIG. 1, illustrating the construction of the bandage strip.

A rolled bandage broadly designated at 10 is illustrated including a foraminous non woven elongated strip material rolled in open width. The elongated strip material has exposed slit edges 11 carried on the strip material. The strip material is formed of continuously extruded filaments 12 of hydrophilic polymer each having portions 12a and 12b extending alternately in both the lengthwise and crosswise directions, respectively. Fused bonded intersections 12 of adjacent lengthwise and cross-wise portions of respective filaments occur at points of engagement of overlying intersection portions. Loops 14 are provided in the filaments between the fused bonded intersections in both the lengthwise and crosswise portions. Thus, slit edges 11 need not be folded and linting is avoided while affording controlled stretchability in the lengthwise and crosswise directions of the strip. The loops 14 are more pronounced in the crosswise portions than in the lengthwise portions affording more stretchability in the crosswise direction than in the lengthwise direction. The hydrophilic polymer is preferably cellulose.

While the drawing illustrates a degree of regularity between bonds at junctures of next adjacent filaments and in the alternation of the lengthwise and crosswise portions, it is to be understood that this is for illustrative purposes only and in practical constructions a degree of randomness necessarily results from the manufacturing technique described herein. A bandage of single thickness is illustrated and preferred but multiple plys are possible where several layers are superimposed, or one or more folds are utilized leaving exposed slit edges and the strip thus formed rolled in open width. It will be observed that stretchability is determined by the extent of the loops between bonded intersections and that such portions have a component in the vertical as well as horizontal planes. Small openings between bonds, as well as stretchability result in better coverage characteristics.

EXAMPLE

A non woven material as described above weighing 33 grams per square meter and slit to 7.5 cm, wide × 285 cm long is wound on a 0.6 cm, spindle using a draft of 1%. The spindle is removed and the diameter of the bandage roll was 4.75 cm. It was undesirably soft for use as a bandage. Softness was measured by noting the diameter when a weight of 200 grams was placed atop a platform contacting the 7.5 cm, wide bandage. Under these conditions the diameter was reduced to 3.10 cm. Roll softness was defined by the formula:

$$\%\text{Softness} = [(d_1 - d_2)/d_1] \times 100$$

where $d_2$ is the diameter under the 100 gm weight and $d_1$ is the unloaded diameter.

The softness as defined by this formula is 35% with a draft of 1% and is considered undesirable for use as a bandage.

A similar experiment was performed with a draft of 3%. Under these conditions the bandage formed had a diameter (dl) of 4.25 cm and its diameter when it supported a 100 gram weight was 3.30 cm. Softness in this case using the above formula is 22%. This is a very satisfactory bandage roll.

If a much harder bandage roll is desired, greater draft may be used and a 10% draft has proven quite satisfactory. Under these conditions the diameter of a bandage similar to the above was 2.5 cm and a 100 gram weight reduced it only to 2.4 cm. This bandage has the advantage that it still retains a large amount of stretch but it occupies less space and requires smaller packaging materials and is, therefore, relatively inexpensive to make. It has been found that drafts above 15% do not increase the hardness of the bandage but they do severely limit its effectiveness. For this reason, the range of 3% draft to 15% is satisfactory.

It is thus observed that a rolled bandage having improved conformability with minimal tendency to lint, having improved coverage and softness may be produced inexpensively.

While a preferred embodiment of the invention has been described using specific terms, such description is for illustrative purposes only, and it is to be understood that changes and variations may be without departing from the spirit or scope of the following claims.

What is claimed is:

1. A rolled bandage comprising:
   a foraminous non woven elongated strip material rolled in open width;
   exposed slit edges carried on said strip material;
   said strip material being formed of spaced continuous extruded filaments of hydrophilic polymer each having portions extending alternately in the lengthwise and crosswise directions;
   fused bonded intersections of adjacent lengthwise and crosswise portions of respective filaments; and
   loops in said filaments between said fused bonded intersections in both lengthwise and crosswise portions;
   whereby slit edges need not be folded and linting is avoided while affording controlled stretchability in the lengthwise and crosswise directions of said strip.

2. The rolled bandage set forth in claim 1 wherein the loops are more pronounced in the crosswise portions than in the lengthwise portions affording more stretchability in the crosswise direction than in the lengthwise direction.

3. The rolled bandage set forth in claim 1 wherein the hydrophilic polymer is cellulose.

4. The rolled bandage set forth in claim 3 wherein the strip is tensioned having been elongated by about 3% to about 15%.

5. The rolled bandage set forth in claim 3 wherein the strip is tensioned having been elongated by at least about 3% and having a weight of from about 20 to about 40 grams per square meter.

* * * * *